(12) United States Patent
Perricone

(10) Patent No.: US 9,034,926 B2
(45) Date of Patent: May 19, 2015

(54) TOPICAL NITRONE SPIN TRAP COMPOSITIONS FOR PSORIASIS

(76) Inventor: Nicholas V. Perricone, Meriden, CT (US)

( * ) Notice: Subject to any disclaimer, the term of this patent is extended or adjusted under 35 U.S.C. 154(b) by 301 days.

(21) Appl. No.: 12/982,221

(22) Filed: Dec. 30, 2010

(65) Prior Publication Data

US 2012/0172452 A1    Jul. 5, 2012

(51) Int. Cl.
     *A61K 31/13*      (2006.01)
     *A61K 31/04*      (2006.01)
     *A61K 31/15*      (2006.01)

(52) U.S. Cl.
     CPC ........................................ *A61K 31/15* (2013.01)

(58) Field of Classification Search
     USPC ........................................ 514/645, 741, 863
     See application file for complete search history.

(56) References Cited

U.S. PATENT DOCUMENTS

| | | | |
|---|---|---|---|
| 4,153,722 A | 5/1979 | Campbell et al. | |
| 4,197,314 A | 4/1980 | Campbell et al. | |
| 4,214,003 A | 7/1980 | Campbell et al. | |
| 4,224,340 A | 9/1980 | Campbell et al. | |
| 4,775,530 A | 10/1988 | Perricone | |
| 5,025,032 A | 6/1991 | Carney et al. | |
| 5,036,097 A | 7/1991 | Floyd et al. | |
| 5,292,746 A | 3/1994 | Carr et al. | |
| 5,376,361 A | 12/1994 | Perricone | |
| 5,397,789 A * | 3/1995 | Carr et al. ..................... | 514/309 |
| 5,405,874 A | 4/1995 | Carney et al. | |
| 5,409,693 A | 4/1995 | Perricone | |
| 5,455,272 A | 10/1995 | Janzen et al. | |
| RE35,112 E | 12/1995 | Carney et al. | |
| RE35,213 E | 4/1996 | Floyd et al. | |
| 5,527,812 A | 6/1996 | Carr et al. | |
| 5,527,828 A | 6/1996 | Janzen et al. | |
| 5,532,252 A | 7/1996 | Carr et al. | |
| 5,532,277 A | 7/1996 | Janzen et al. | |
| 5,545,398 A | 8/1996 | Perricone | |
| 5,574,063 A | 11/1996 | Perricone | |
| 5,643,586 A | 7/1997 | Perricone | |
| 5,677,315 A | 10/1997 | Carr et al. | |
| 5,681,845 A | 10/1997 | Janzen et al. | |
| 5,681,965 A | 10/1997 | Carney et al. | |
| 5,709,868 A | 1/1998 | Perricone | |
| 5,879,690 A | 3/1999 | Perricone | |
| 5,942,507 A | 8/1999 | Kelleher et al. | |
| 5,965,618 A | 10/1999 | Perricone | |
| 6,002,001 A * | 12/1999 | Carney et al. ..................... | 544/56 |
| RE36,594 E | 2/2000 | Janzen et al. | |
| 6,051,571 A | 4/2000 | Kelleher et al. | |
| 6,191,121 B1 * | 2/2001 | Perricone ........................ | 514/78 |
| 6,255,353 B1 * | 7/2001 | Waterbury et al. ............ | 514/643 |
| 6,291,702 B1 | 9/2001 | Becker | |
| 6,376,540 B1 | 4/2002 | Kelleher et al. | |
| 6,979,459 B1 * | 12/2005 | Perricone ...................... | 424/443 |
| 6,998,419 B2 * | 2/2006 | Waterbury et al. ............ | 514/476 |
| 2008/0167474 A1 | 7/2008 | Becker et al. | |
| 2009/0258841 A1 * | 10/2009 | Murphy et al. ............... | 514/125 |
| 2010/0168112 A1 | 7/2010 | Kelly et al. | |

OTHER PUBLICATIONS

Kurd et al. Expert Rev. Clin. Immunol., 2007; 3(2) pp. 171-185.*
MacDonald et al, Postgrad Med J, 2007; vol. 83, pp. 690-697.*
Rashmi, et al.; "A Comprehensive Review of Biomarkers in Psoriasis"; Clin Exp Dermatol; Aug. 2009; Abstract only (one page).
Tekin, et al.; "Accumulation of Oxidized Low-Density Lipoprotein in Psoriatic Skin and Changes of Plasma Lipid Levels in Psoriatic Patients"; Hindawi Publishing Corporation; Mediators of Inflammation; 2007; 5 pages.
Aleynik, et al.; "Dilinoleoylphosphatidylcholine is the active antioxidant of polyenylphosphatidylcholine."; J Invesig. Med. Nov. 1999; 47(9); pp. 507-512 (one page abstract only).
Rana; "Electron Paramagnetic Resonance Spectroscopy in Radiation Research: Current Status and Perspectives", J. Pharmacy & BioAllied Sciences, 2, 8 pages (2010).
International Search Report and Written Opinion of the International Searching Authority; Application No. PCT/US2011/068147; Issued: Apr. 23, 2012; Mailing Date: May 2, 2012; 10 pages.
Cooke; "Oxidative DNA Damage: Mechanisms, Mutation, and Disease"; the FASEB Journal, 17, 1195-1214 (2003).
Qiang Zhou, "Oxidative Stress in the Pathogenesis of Psoriasis"; Free Radical Biology & Medicine, 47: abstract; 3 pages (2009).

\* cited by examiner

*Primary Examiner* — Paul Zarek
*Assistant Examiner* — George W Kosturko
(74) *Attorney, Agent, or Firm* — St. Onge Steward Johnston & Reens LLC

(57) ABSTRACT

Psoriasis is treated by application of a composition containing a nitrone spin trap such as α-phenyl t-butyl nitrone (PBN) and derivatives thereof. Preferred compositions and method of treatments further comprise at least one adjunctive ingredient including fatty acid esters of ascorbic acid such as ascorbyl palmitate and ascorbyl stearate, and polyenylphosphatidylcholine.

8 Claims, No Drawings

TOPICAL NITRONE SPIN TRAP COMPOSITIONS FOR PSORIASIS

FIELD OF THE INVENTION

The present invention relates to the skin disease known as psoriasis and, more particularly, to nitrone spin trap compositions and methods of use thereof for the treatment of psoriasis.

BACKGROUND OF THE INVENTION

Psoriasis is a lifelong skin disease that occurs when faulty signals in the immune system cause skin cells to regenerate too quickly, on the order of every three to four days instead of the usual 30-day cycle. Extra skin cells build up on the skin's surface, forming red, flaky, scaly lesions that can itch, crack, bleed and be extremely painful. Psoriasis generally involves the joints, limbs and scalp but it can appear anywhere on the body, covering some people from head to toe. More than 7 million Americans have been diagnosed with psoriasis and/or psoriatic arthritis, a degenerative disease of the joints and connective tissues associated with psoriasis. Psoriasis typically first strikes people between the ages of 15 and 35, but can affect anyone at any age, including children.

Psoriasis is characterized by erythematous eruptions, often in papules or plaques, and usually having a white, silvery scale. Psoriasis is generally considered an inflammatory skin condition. Other inflammatory skin conditions include atopic dermatitis (eczema), seborrhoeic dermatitis, rosacea, acne, as well as contact dermatitis (typically arising from allergic reaction to poison ivy and other allergens).

Psoriasis is persistent and unpredictable in its course. The exact etiology of psoriasis is unknown. It is postulated that psoriasis may involve abnormalities in essential fatty acid metabolism, free radical generation, lipid peroxidation, and/or release of lymphokines. One study showed that lipid peroxidation mediated by free radicals is one of the important causes of cell membrane destruction and cell damage associated with psoriasis. Tekin N. S., Accumulation of oxidized low-density lipoprotein in psoriatic skin and changes of plasma lipid levels in psoriatic patients, *Mediators Inflamm.* 12, 78454 (2007). Other studies also reported that oxidative stress and increased free-radical generation link to psoriasis. Rashmi R, *Clin. Exp. Dermatol.* 34, 658-63 (2009); Cooke, M. S., Oxidative DNA damage: mechanisms, mutation, and disease, *the FASEB Journal,* 17, 1195-1214 (2003).

Despite a voluminous scientific literature and numerous treatment strategies, there is still no effective treatment for psoriasis that is completely without side effects. Conventional therapeutic regimens for psoriasis include topical or intralesional application of corticosteroids, anthralin, tazarotene (a retinoid), acitretin (a second-generation retinoid), calcipotriene (vitamin D3) and/or zinc compounds, and/or selenium compounds, and/or coal tar compounds; or various light therapies; or an oral or injected systemic agent. No single therapy is ideal, and it is rare for a patient not to be treated with several alternatives during the relapsing and remitting course of the disease. Whereas systematic treatment can induce prompt resolution of psoriatic lesions, suppression often requires ever-increasing doses, sometimes with toxic side effects, and tapering of therapy may result in rebound phenomena with extensions of lesions, possibly to exfoliation. Other inflammatory skin conditions are typically treated with the same types of therapies.

As set forth in more detail hereafter, the present invention is based on the topical use of nitrone spin trap compositions as a treatment for psoriasis and other inflammatory skin conditions.

Nitrone spin traps are potent free radical scavengers and antioxidants, and are commonly used as analytical tools to study free radicals. Nitrones behave as spin trapping agents when a diamagnetic nitrone compound (the "spin trap") reacts with a transient free radical species (having the "spin") to provide a relatively more stable radical species (referred to as the "spin adduct"). The spin adduct may be detectable by electron paramagnetic resonance (EPR) spectroscopy, or electron spin resonance (ESR) if the spin adduct has a reasonable lifetime. Thus, spin trapping allows previously unobservable free radicals to be identified and studied using ESR, EPR, and related techniques. Sudha Rana, Electron paramagnetic resonance spectroscopy in radiation research: Current status and perspectives, *J. Pharmacy & BioAllied Sciences,* 2, 80-87 (2010).

The use of nitrones as spin traps for studying unstable free radicals has been applied to biological systems. In this regard, α-phenyl t-butyl nitrone (PBN), 5,5-dimethylpyrroline N-oxide (DMPO) and related compounds have been used to identify superoxide ($O_2$.) and hydroxyl radicals (HO.) in biological systems. Additionally, such nitrones have been used to study lipid peroxidation and other free radical-induced biological processes.

Besides serving as research aids or diagnostic tools, nitrone spin traps are extremely therapeutic. For example, PBN and derivatives thereof, have been reported for the treatment of a wide variety of disease conditions arising from or characterized by free radical-induced oxidative damage. Such disease conditions include, for example, disorders of the central nervous system (CNS) and the peripheral nervous system, such as stroke, Parkinsonism, traumatic nerve damage and the like, and disorders of the peripheral organs, such as atherosclerosis, cardiac infarction, ulcerative colitis and the like. Nitrones have also been reported to treat certain inflammatory conditions, such as arthritis.

It would be desirable to have an effective treatment for psoriasis, particularly via a topical administration of an efficient free radical scavenger such as nitrone spin traps.

To be an effective topical therapeutic agent for treating psoriasis, it is desirable to be able to administer the nitrone spin traps at high doses, especially initially, to the localized area surrounding the psoriasis plague, to minimize the amount of free radical-induced oxidative damage that occurs. Thus, the nitrone spin traps used to treat psoriasis conditions should be non-toxic or have very low toxicity.

It is also important that the nitrone spin traps have sufficient solubility at the biological site where the free radicals are generated so that the radicals are trapped by the nitrone spin traps before they are quenched or cause oxidative damage by their surroundings. Thus, it would be particularly desirable to be able to optimize the solubility of the nitrone spin traps from aqueous to lipophilic.

It is further desirable that the nitrone spin traps either be stable per se or have the ability to be stabilized in admixture with other components, so that preparations can be marketed with a suitably long shelf-life and such that prolonged activity can be obtained once topical application has been made.

Accordingly, a need exists for nitrone spin traps having low toxicity, increased solubility, and long shelf-life for the effective topical treatment of psoriasis.

SUMMARY OF THE INVENTION

The primary object of this invention is to provide a treatment for psoriasis, and more particularly, to provide a therapy based upon topical application to affected skin areas of an active agent, preferably in association with a dermatologically acceptable carrier or vehicle.

This and other objectives of the invention are accomplished by the present invention, which provides a nitrone spin trap, preferably PBN and derivatives, which is topically applied to exposed or affected skin areas, for the treatment and prevention of psoriasis, often in association with a dermatologically acceptable carrier. The amount of the nitrone spin trap necessary to bring about the therapeutic treatment of psoriasis is not fixed per se, and necessarily is dependent upon the severity and extent of the disease, the form of the nitrone spin trap employed, and the concentration of the nitrone spin trap when employed in association with a carrier.

The composition contains from about 1 w/w % to about 40 w/w % of the nitrone spin trap, preferably between about 3 w/w % to about 20 w/w %. In one embodiment, the quantity of the nitrone spin trap will range between about 10 w/w % to about 40 w/w %.

The composition may further comprise at least one adjunct ingredient such as fatty acids, fatty acid esters of ascorbic acid, and polyenylphosphatidylcholine. The amount of each adjunct ingredient is at a range of about 0.025 w/w % to about 0.5 w/w %.

DETAILED DESCRIPTION OF THE INVENTION

Compositions containing nitrone spin trap according to the present invention are topically applied to and absorbed by the skin tissue for the treatment of psoriasis and other skin inflammatory diseases. Topical administration of nitrone spin trap has the advantage of directly acting on the areas of the damaged skin and avoiding the problem of breakdown into constituent components that occurs in oral administration of nitrone spin trap.

As used herein, the term "nitrone spin trap(s)" used herein and after refers to both nitrone spin traps and derivatives thereof.

Any nitrone spin traps, either in straight chain or in cyclic configuration, may be employed in compositions of the invention. Common nitrone spin traps can typically be purchased from Sigma-Aldrich Chemical Co. or other chemical vendors. Uncommon nitrone spin traps, for example, azulenyl nitrone spin traps and furan nitrone spin traps, can be synthesized following the procedures known in the art. U.S. Pat. No. 6,376,540 to Kelleher and U.S. Pat. App. No. 20080167474 to Becker have reported the synthesis of these types of nitrone spin traps, the disclosure of which is incorporated by references in entirety. Regardless the source of the spin traps, it is important that the spin traps are sufficiently pure, ideally with greater than 98% purity, and any impurities should be inert in the sense of not bringing about a deactivation of the nitrone spin traps. Preferred spin traps should have minimal or no toxicity to normal cells. Suitable nitrone spin traps include, but is not limited to, phenyl N-tert-butylnitrone, also referred to as α-phenyl t-butyl nitrone (PBN), 5,5-dimethylpyrroline N-oxide (DMPO), α-(4-pyridyl 1-oxide)-N-tert-butylnitrone (POBN), 3,3,5,5-tetramethyl-1-pyrroline N-oxide, and 2,4,4,6-tri-tert-butylnitrosobenzene (BNB). Other nitrone spin traps described in U.S. Pat. Nos. 5,405,874, 5,681,845, 5,681,965, 6,002,001 and RE. 36,594 can also be used, the disclosure of which is incorporated herein by reference.

The most preferred nitrone spin traps are PBN and derivatives thereof, because they have no measurable effect on normal or uninjured cells. PBN and derivatives thereof have the following general formula:

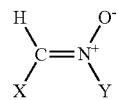

wherein X is phenyl or substituted phenyl with up to five substitutions on the phenyl ring, and each substitution is independently (can vary within the molecule) selected from the group consisting of hydrogen, halogen, alkyl, substituted alkyl, alkaryl, alkoxyl, alkenyl, and amino; and Y is selected from the group consisting of alkyl, substituted alkyl, alkenyl, alkynyl, naphthyl, heterocyclic, alkcycloalkyl, cycloalkyl and cycloalkenyl.

"Alkyl" refers to monovalent alkyl groups preferably having from 1 to about 12 carbon atoms, more preferably 1 to 8 carbon atoms and still more preferably 1 to 6 carbon atoms. This term is exemplified by groups such as methyl, ethyl, n-propyl, isopropyl, n-butyl, isobutyl, tert-butyl, n-hexyl, n-octyl, tert-octyl and the like.

"Amino" refers to primary, secondary and tertiary alkyl substituted amino groups and the like.

"Substituted alkyl" refers to an alkyl group preferably having from 1 to about 12 carbon atoms, more preferably 1 to 8 carbon atoms and still more preferably 1 to 6 carbon atoms, which is substituted with from 1 to 3 substituents selected from the group consisting of alkoxy, amino, mono- and dialkylamino, aminoacyl, aminocarbonyl, alkoxycarbonyl, aryl, carboxyl, cyano, halo, heterocyclic, hydroxy, nitro, thioalkoxy and the like. A preferred substituted alkyl group is the trifluoromethyl group.

"Alkaryl" refers to alkylene-aryl groups preferably having from 1 to 10 carbon atoms in the alkylene moiety and from 6 to 14 carbon atoms in the aryl moiety. Such alkaryl groups are exemplified by benzyl, phenethyl, and the like.

"Alkcycloalkyl" refers to -alkylene-cycloalkyl groups preferably having from 1 to 10 carbon atoms in the alkylene moiety and from 3 to 8 carbon atoms in the cycloalkyl moiety. Such alkcycloalkyl groups are exemplified by cyclopropyl, cyclopentyl, cyclohexyl, and the like.

"Alkoxy" refers to the group "alkyl-O—". Preferred alkoxy groups include, by way of example, methoxy, ethoxy, n-propoxy, isopropoxy, n-butoxy, tert-butoxy, sec-butoxy, n-pentoxy, n-hexoxy, 1,2-dimethylbutoxy, and the like.

"Alkenyl" refers to alkenyl groups preferably having from 2 to 10 carbon atoms and more preferably 2 to 6 carbon atoms and having at least 1 and preferably from 1-2 sites of alkenyl unsaturation. Preferred alkenyl groups include ethenyl, n-propenyl, isopropenyl, and the like.

"Alkynyl" refers to alkynyl groups preferably having from 2 to 10 carbon atoms and more preferably 2 to 6 carbon atoms and having at least 1 and preferably from 1-2 sites of alkynyl unsaturation. Preferred alkynyl groups include ethynyl, propargyl, and the like.

"Cycloalkyl" refers to cyclic alkyl groups of from 3 to 10 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as adamantanyl, and the like.

"Cycloalkenyl" refers to cyclic alkenyl groups of from 4 to 10 carbon atoms having a single cyclic ring and at least one point of internal unsaturation which can be optionally substituted with from 1 to 3 alkyl groups. Examples of suitable cycloalkenyl groups include, for instance, cyclopent-3-enyl, cyclohex-2-enyl, cyclooct-3-enyl and the like.

"Halo" or "halogen" refers to fluoro, chloro, bromo and iodo. Preferred halo groups are either fluoro or chloro.

"Heterocycle" or "heterocyclic" refers to a monovalent saturated or unsaturated group having a single ring or multiple condensed rings, from 1 to 10 carbon atoms and from 1 to 4 hetero atoms selected from nitrogen, sulfur or oxygen within the ring. Examples of heterocycles include, but are not limited to, morpholine, piperazine, imidazolidine, pyrrolidine, piperidine and the like.

"Naphthyl" refers to naphthyl ring and can optionally be substituted with from 1 to 3 substituents selected from the group consisting of alkyl, substituted alkyl, alkoxy, alkenyl, alkynyl, amino, aminoacyl, aminocarbonyl, alkoxycarbonyl, aryl, carboxyl, cyano, halo, hydroxy, nitro, trihalomethyl and the like.

For the spin traps that are fat-soluble, such as azulenyl nitrones, their preparations can be applied neat to skin tissue. The fatty nitrone spin traps also have an advantage of lubricating the affected skin areas to which they are applied.

However, only effective amounts of nitrone spin traps are needed to treat psoriasis, so generally topical application to exposed or affected skin sites is accomplished in association with a carrier, even for the fatty nitrone spin traps. A suitable carrier should be one in which nitrone spin traps is soluble per se or is effectively solubilized (e.g., as an emulsion or microemulsion). Where employed, the carrier is inert in the sense of not bringing about a deactivation or oxidation of the nitrone spin traps, and in the sense of not bringing about any adverse effect on the skin areas to which it is applied.

In one preferred practice of the invention, nitrone spin traps are applied in admixture with a dermatologically acceptable carrier or vehicle (e.g., as a lotion, cream, ointment, soap, stick, or the like) so as to facilitate topical application and, in some cases, provide additional therapeutic effects as might be brought about, e.g., by moisturizing of the affected skin areas. While the nitrone spin trap carrier for dermatological compositions can consist of a relatively simple solvent or dispersant such as water, it is generally preferred that the carrier comprises a composition more conducive to topical application, and particularly one which will form a film or layer on the skin to which it is applied so as to localize the application and provide some resistance to washing off by immersion in water or by perspiration and/or aid in the percutaneous delivery of the active agent. Suitable carriers include water, alcohols, oils and the like, chosen for their ability to dissolve or disperse the nitrone spin traps and any other ingredients used in the treatment. Preferably, the carrier is made of phospholipid, and more preferably, made of lecithin.

Many preparations are known in the art, and include lotions containing oils and/or alcohols and emollients such as hydrocarbon oils and waxes, silicone oils, vegetable, animal or marine fats or oils, glyceride derivatives, fatty acids or fatty acid esters or alcohols or alcohol ethers, lecithin, lanolin and derivatives, polyhydric alcohols or esters, wax esters, sterols, phospholipids and the like, and generally also emulsifiers (nonionic, cationic or anionic), although some of the emollients inherently possess emulsifying properties. These same general ingredients can be formulated into a cream rather than a lotion, or into gels, or into solid sticks by utilization of different proportions of the ingredients and/or by inclusion of thickening agents such as gums or other forms of hydrophilic colloids. One preferred embodiment is an oil-in-water cream. Such compositions are referred to herein as dermally or dermatologically acceptable carriers. Other materials as well as processing techniques and the like are set forth in *Remington's Pharmaceutical Sciences,* 17$^{th}$ edition, 1985, Mack Publishing Company, Easton, Pa., which are incorporated by reference.

The quantity of the nitrone spin trap in the carrier may be varied or adjusted widely depending upon the particular application, the potency of the particular compound, and the desired concentration. Generally, it is contemplated that the present invention will deliver the nitrone spin trap to the skin at a very high concentration during initial treatment and gradually titration down to a low concentration maintenance dose. The quantity of the nitrone spin trap may range between about 1% to about 40% by weight of the composition, preferably between about 3% to about 20% by weight of the composition. In one embodiment, the quantity of the nitrone spin trap will range between about 10% to about 40% by weight of the composition.

In the practice of methods of the invention, the composition is topically applied to the skin areas affected by psoriasis, at predetermined intervals often as a lotion or the like, it generally being the case that gradual improvement is noted with each successive application.

Some embodiments of this invention contain at least one other adjunct ingredient in addition to the nitrone spin trap. Adjunct ingredients include, but are not limited to, fatty acids, which may be in the form of fatty acid esters, and polyenylphosphatidylcholine. Many embodiments employ more than one adjunct ingredient.

As used herein, the term "fatty acid" has reference to and encompasses the all isomers of the free acid and structurally related, biologically equivalent derivatives such as salts and esters. Suitable fatty acids include, but not limited to, long chain fatty acids such as lipoic acid and ascorbic acid, essential fatty acids, such as omega-3 fatty acid, linoleic acid, and omega-6 fatty acid, arachidonic acid.

The most preferred fatty acid is ascorbic acid (vitamin C), which is often employed in the form of fat-soluble fatty acid esters of ascorbic acid. The more oxidation-resistant saturated fatty acid esters of ascorbic acid are preferred, including, but not limited to, ascorbyl laurate, ascorbyl myristate, ascorbyl palmitate, ascorbyl stearate, and ascorbyl behenate. Ascorbyl palmitate is used in one embodiment. As denoted herein, where fatty acid esters are described, e.g., ascorbyl stearate, compositions having predominantly that ester, e.g., predominantly ascorbyl stearate, are included. The esters may be prepared using hydrogenated oils or fats, or fractions thereof, and contain small amounts of another ester. Ascorbyl stearate prepared using canola, for example, commonly contain about 4% ascorbyl palmitate. It is an advantage of the invention that where fatty acid esters of ascorbic acid are employed as an adjunct ingredient, they help stabilize and solubilize the nitrone spin trap in the composition.

Polyenylphosphatidylcholine (PPC) is employed as an adjunct ingredient in other embodiments, alone or in combination with the fatty acids. By "polyenylphosphatidylcholine" it meant any phosphatidylcholine (PC) bearing two fatty acid substituents, wherein at least one is an unsaturated fatty acid with at least two double bonds. Preferred polyenylphosphatidylcholines contain at least one linoleic (18:2) group, most preferably two, in a cis geometrical configuration typical of natural products, which presents in the preparation at levels of at least about 25%, preferably at least about 40% by weight. Other forms of PPC can also be used as those set out in U.S. Pat. No. 6,797,459 at column 3 lines 34 to 52. PPC itself is an active antioxidant that has been shown to protect against lipid peroxidation and liver damage, including fibrosis and cirrhosis (Aleynik, S. I., et al., *J. Investig. Med.* 47: 507-512 (1999)). Moreover, because PC itself is a major constituent of cell membranes, PPC readily penetrates skin and disperses in cell membranes. Thus, when employed, PPC greatly enhances the antioxidant activity of the composition because it facilitates the nitrone spin traps to penetrate into psoriatic lesions in quantities sufficient to reach therapeutic levels.

Where adjunct ingredients are employed, the amount of adjunct ingredients necessary to bring about enhanced prevention and/or therapeutic skin treatment in conjunction with the nitrone spin trap is not fixed per se, and necessarily is dependent upon the identity and form of the adjunct ingredients employed, the concentration of the adjunct ingredients when employed with a carrier, the user's skin type, and, where present, the severity and extent of the patient's pathological skin condition. Since PBN degrades at pH less than approximately 3 to 4, it is important that the amount of the fatty acid or other ingredients added would not bring the composition to a pH below 4. Many embodiments contain from about 0.025% to 0.5% of the fatty acid or esters thereof, and/or from about 0.025% to 0.5% of the PPC. Generally, the nitrone spin trap composition with the adjunct ingredient(s) is topically applied in effective amounts to skin areas which have been damaged by psoriasis or other skin inflammation.

The mechanisms of action of the therapeutic effectiveness of the nitrone spin traps for psoriasis are not fully understood at this time. One theory is that phenyl butyl nitrones reduce levels of the free radicals, especially hydroxyl and superoxide radicals that implicate psoriasis, by forming stable complexes with the free radicals, thus inhibit the lipoxygenase oxidation pathway and interrupt the inflammatory cascade processes which result in the regulation of the cell growth cycle. Accordingly, skin cells are produced in a normal manner instead of the accelerated and damaged state typical of psoriasis and other inflammatory skin conditions.

This theory can be supported, in part, by the fact that the nitrone spin traps, such as PBN and derivatives, have little or no measurable effect on normal cells. A rational explanation is that stable complexes are formed between free radicals and nitrone spin traps during the treatment. Because nitro spin traps can only react with the free radicals produced by those damaged cells, normal cells with no free radicals could not be affected by nitrone spin traps.

However, the high efficiency of the present invention in the treatment of psoriasis suggests that phenyl butyl nitrones may function beyond their antioxidant capabilities. Without wishing being bound by theory, it is believed that phenyl butyl nitrones act as Michael acceptor pharmacophores in binding to, and thus inactivating, the transcription factors which contribute to the pathogenesis of psoriasis. This mechanism of action is proposed based on the chemical structure of phenyl butyl nitrones which have a chemical structure in which an active nitrogen atom is adjacent an oxygen atom, so that the carbon atom next to the nitrogen becomes electron deficient. This allows phenyl butyl nitrones to act as electrophilic Michael acceptors to bind with the cysteine residues on many different enzyme genera and transcription factors. Since the Michael reaction is irreversible, phenyl butyl nitrones thus permanently inhibit the cellular signal transduction pathways that lead to psoriatic lesions.

It has recently been proposed that a positive feedback loop is involved in psoriatic lesions that strengthens the effect of Reactive Oxygen Species (ROS) and amplifies the production of proinflammatory cytokines: (1) ROS trigger activation of MAPK/AP-1, NF-κB, and JAK-STAT signaling pathways, which subsequently induce iNOS, and (2) ONOO— is generated by the reaction of NO and oxidant $O_2$.—, resulting in the activation of NF-κB and AP-1, which evoke the expression of the target genes. Qiang Zhou, Oxidative stress in the pathogensis of psoriasis, *Free Radical Biology & Medicine*, 47: 891-905 (2009).

Phenyl butyl nitrones should bind to and inactivate NF-kB, a molecule which is significantly expressed in psoriatic skin and which up-regulates over one hundred proinflammatory compounds including those implicated in the development of psoriatic lesions. Moreover, phenyl butyl nitrones should bind to and inactivate transcription factor AP-1. As a consequence, the effect of the phenyl butyl nitrones should be to inhibit the primary cellular signal transduction pathways that lead to psoriatic lesions and therefore provide for prevention and treatment of psoriasis.

In addition, phenyl butyl nitrones should also activate Nrf2, a transcription factor which up regulates about twenty different cyto protective enzymes, phase 2 proteins and antioxidant enzymes, thus inhibiting NO production and providing a secondary pathway for prevention and treatment of psoriasis.

The above described mechanisms of action mean that relatively small amounts of phenyl butyl nitrones are sufficient for effective prevention and treatment of psoriasis. By inactivating the key transcription factors at an early stage of the pathogenesis pathways, phenyl butyl nitrones block the signal transduction pathways, and prevent the subsequent cascading, catalytic, and up-regulated expression of proinflammatory cytokines and chemokines in the psoriasis stage. The high efficacy of phenyl butyl nitrones is a particularly beneficial aspect of the present invention.

Methods and compositions of the present invention are also useful for treating other type of inflammatory skin conditions, such as dermatitis, rosacea, seborrhea, eczema, xerosis (dry skin), thermal and radiation burns. It is an advantage of the invention that topical application of nitrone spin traps provides a simple, non-invasive, nontoxic, over-the-counter topical method for treating all kinds of skin damages, including psoriasis. It is a further advantage of the invention that nitrone spin trap is particularly efficacious in the treatment of certain skin conditions that do not respond to topical corticosteroids.

All references cited herein are hereby incorporated by reference, as are additional ingredients and methods set out in U.S. Pat. Nos. 4,775,530, 5,376,361, 5,409,693, 5,545,398, 5,574,063, 5,643,586, 5,709,868, 5,879,690, 5,965,618, 5,968,618, 6,191,121, and 6,979,459. Generally, these compositions contain other active ingredients summarized above that enhance the effect of active ingredients of the invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims.

What is claimed is:
1. A method for the treatment of psoriasis, comprising: topically applying to the affected skin areas a topical composition comprising:
about 1% to about 40% by weight of a nitrone spin trap having the chemical structure of:

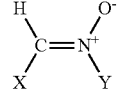

wherein
- X is phenyl or substituted phenyl with up to five substitution groups on the phenyl ring, wherein each said substitution groups is independently selected from the group consisting of hydrogen, halogen, alkyl, substituted alkyl, alkaryl, alkoxyl, alkenyl, and amino, and
- Y is selected from the group consisting of alkyl, substituted alkyl, alkenyl, alkynyl, naphthyl, heterocyclic, alkcycloalkyl, cycloalkyl and cycloalkenyl;
- 0.25% to about 0.5% by weight of polyenylphosphatidylcholine; and
- a dermatologically acceptable lecithin carrier.

2. The method according to claim 1, wherein said composition contains from about 3% to about 20% of said nitrone spin trap by weight of the composition.

3. The method according to claim 1, wherein said composition contains from about 10% to about 40% of said nitrone spin trap by weight of the composition.

4. The method according to claim 1, wherein said carrier is a solution, dispersion, cream, lotion, gel or solid stick.

5. The method according to claim 1, wherein said nitrone spin trap is a-phenyl-tert-butylnitrone.

6. The method according to claim 1, wherein dilinoleoylphosphatidylcholine is the most abundant phosphatidylcholine species in said polyenylphosphatidylcholine component of the composition.

7. The method according to claim 6, wherein dilinoleoylphosphatidylcholine comprises at least about 25% by weight of said polyenylphosphatidylcholine.

8. The method according to claim 7, wherein dilinoleoylphosphatidylcholine comprises at least about 40% by weight of said polyenylphosphatidylcholine.

* * * * *